United States Patent
Fortenberry et al.

(10) Patent No.: US 8,206,594 B2
(45) Date of Patent: Jun. 26, 2012

(54) FLUID MANAGEMENT SYSTEM FOR ACCURATE CONTINUOUS HEMOFILTRATION IN EXTRACORPOREAL MEMBRANE OXYGENATION (ECMO)

(75) Inventors: James D. Fortenberry, Atlanta, GA (US); Ajit P. Yoganathan, Tucker, GA (US); Philippe Sucosky, South Bend, IN (US); Lakshmi Prasad Dasi, Fort Collins, CO (US); Matthew L. Paden, Stone Mountain, GA (US)

(73) Assignees: Emoery University, Atlanta, GA (US); Children's Healthcare of Atlanta, Atlanta, GA (US); Georgia Tech Research Corporation, Atlanta, GA (US)

( * ) Notice: Subject to any disclaimer, the term of this patent is extended or adjusted under 35 U.S.C. 154(b) by 133 days.

(21) Appl. No.: 12/663,253

(22) PCT Filed: Jun. 6, 2008

(86) PCT No.: PCT/US2008/066108
§ 371 (c)(1),
(2), (4) Date: Jun. 9, 2010

(87) PCT Pub. No.: WO2008/154376
PCT Pub. Date: Dec. 18, 2008

(65) Prior Publication Data
US 2010/0288703 A1 Nov. 18, 2010

Related U.S. Application Data

(60) Provisional application No. 60/942,218, filed on Jun. 6, 2007.

(51) Int. Cl.
*B01D 61/32* (2006.01)
*B01D 61/28* (2006.01)
*B01D 61/22* (2006.01)
*B01D 61/18* (2006.01)
*A61M 1/34* (2006.01)

(52) U.S. Cl. ........ 210/646; 210/645; 210/650; 210/651; 210/739; 210/740; 210/744; 210/85; 210/86; 210/97; 210/103; 210/104; 210/109; 210/143; 210/252; 210/257.1; 210/257.2; 210/258; 604/4.01; 604/5.01; 604/5.04; 604/6.04; 604/6.09; 604/6.1; 604/6.11; 604/6.15; 604/29; 604/30

(58) Field of Classification Search ............ 210/645, 210/646, 650, 651, 739, 740, 744, 85, 86, 210/97, 103, 104, 109, 143, 252, 257.1, 257.2, 210/258; 604/4.01, 5.01, 5.04, 6.04, 6.1, 604/6.11, 6.15, 28, 29, 30
See application file for complete search history.

(56) References Cited

U.S. PATENT DOCUMENTS

| | | |
|---|---|---|
| 5,306,510 A | 4/1994 | Meltzer |
| 2004/0245161 A1 | 12/2004 | Treu et al. |
| 2005/0281809 A1 | 12/2005 | Roberts et al. |
| 2006/0184084 A1 | 8/2006 | Ware et al. |

*Primary Examiner* — John Kim
(74) *Attorney, Agent, or Firm* — Randi Beth Isaacs; Susanne Hollinger; Emory Patent Group

(57) ABSTRACT

A novel system and method for fluid management for accurate continuous venovenous hemofiltration (CWH) in extracorporeal membrane oxygenation (ECMO). The fluid management or CWH system is automated and configured for operation as a stand alone unit and can be easily integrated with an ECMO system. The fluid management system is capable of producing either perfect or negative fluid balance between ultrafiltrate removal and replacement fluid delivery. The fluid management system can achieve electrolyte replacement over a range of flow rates needed to care for patients ranging from neonates to adults. Finally, the novel fluid management system preserves patient safety, maintains sterility during operation, is easy to operate, and is compact enough to fit near a patient's bed.

18 Claims, 14 Drawing Sheets

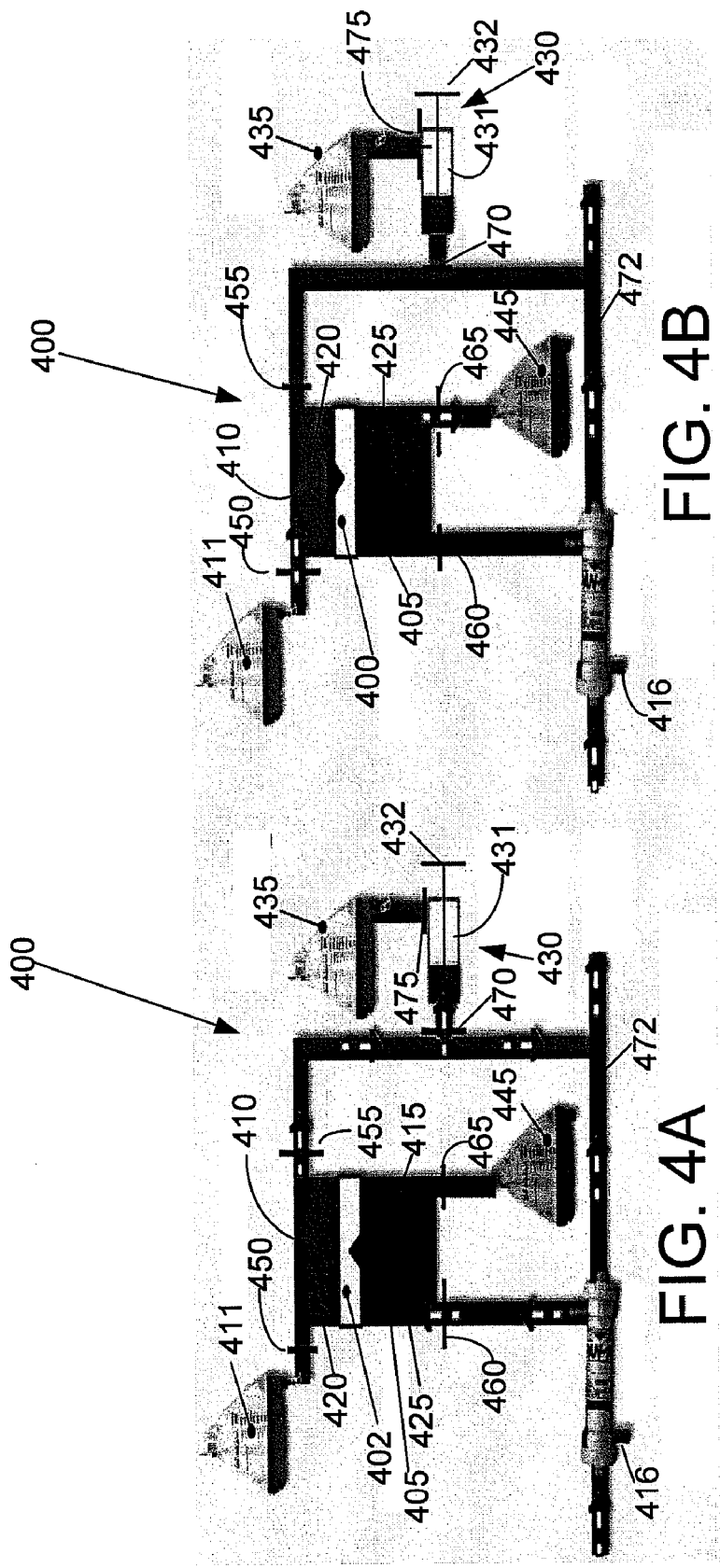

FLUID MANAGEMENT SYSTEM FOR ACCURATE CONTINUOUS HEMOFILTRATION IN EXTRACORPOREAL MEMBRANE OXYGENATION (ECMO)

CROSS-REFERENCE TO RELATED APPLICATIONS

This application is a National Stage Application of PCT/US2008/066108, filed 6 Jun. 2008, in the name of Georgia Tech Research Corporation, a U.S. national corporation, applicant for all countries except the US, and Philippe Sucosky, a citizen of France, Lakshmi Prasad Dasi, a citizen of India, and Ajit P. Yoganathan, James D. Fortenberry, and Matthew L. Paden, all citizens of the U.S., applicants for the designation of the US only, and which claims benefit of United States provisional patent application Ser. No. 60/942,218 filed Jun. 6, 2007, and which applications are incorporated herein by reference. To the extent appropriate, a claim of priority is made to each of the above disclosed applications.

FIELD OF INVENTION

The present invention relates to systems and methods for fluid management in critically ill patients. More particularly, the present invention relates to systems and methods for fluid management that is continuous, automated, and accurate for treatment of critically ill patients who also require extracorporeal membrane oxygenation treatment.

BACKGROUND OF THE INVENTION

Extracorporeal life support (ECLS) is a widely used technique in intensive care units to assist patients with severe organ deficiencies. Among the different ECLS techniques, extracorporeal membrane oxygenation (ECMO) provides life-saving temporary heart and lung support to patients who experience cardiac and/or respiratory failure unresponsive to standard ventilator and pharmacologic management. The clinical implementation of ECMO varies, but generally consists of a drain cannula through which blood is drained from the patient's venous system, a roller or centrifugal pump, a membrane oxygenator that oxygenates the blood and removes carbon dioxide, a bladder pressure module, a heat exchanger, and an arterial cannula through which the oxygenated blood is returned to the patient's arterial system.

Although the implementation of ECMO in the neonatal, pediatric and adult intensive care unit has been shown to result in improved survival rates, it is also associated with some complications. Patients treated with ECMO may experience acute renal failure due to combined renal hypoperfusion and hypoxemia as a result of their primary disease, resulting ultimately to a decreased urine output. Since illnesses leading to cardio respiratory failure can require large volumes of fluid resuscitation, patients often received large amounts of crystalloid and blood products during their pre-ECMO course and may develop serious fluid overload. This fluid overload is associated with pulmonary edema, worsening lung injury, and increased incidence of multiple organ failure in critically ill patients. Recent studies have suggested that improved fluid balance could be associated with improved outcomes in critically ill patients. Fluid restriction can be employed in management; however this is often at the expense of decreasing caloric intake, which could be detrimental to improving overall outcomes. Treating or preventing fluid overload in this setting can require aggressive use of diuretics, which has been suggested to worsen outcomes in critically ill adults with renal failure.

Renal support can be provided by a continuous renal replacement therapy (CRRT) such as continuous venovenous hemofiltration (CVVH). This technique allows for precise control of fluid balance by providing continuous fluid, electrolyte and toxin clearance even in the absence of adequate native renal function via convective processes through a permeable membrane. The hemofiltration retains proteins and cellular components of the intravascular space and eliminates plasma water and dissolved solutes. A typical CVVH setup consists of a hemofilter and a pair of pumps to achieve the drainage of the ultrafiltrate which is discarded and the delivery of replacement fluid, respectively. The portion of the ultrafiltrate that corresponds to body weight loss within a patient is discarded merely as removal filtrate. However, when the excess of the ultrafiltrate other than the removal filtrate is discarded, blood that has been filtered must be given a replacement fluid in an amount equal to the amount of the excess to maintain the water balance of the patient. It is known that most optimally the living body should be given replacement fluid continuously at the same rate as the discharge of the excess of ultrafiltrate. To meet these requirements, it is critical for CVVH systems to measure the amounts of the ultrafiltrate, excess ultrafiltrate and replacement fluid.

To supply the replacement fluid continuously in balance with the excess ultrafiltrate, systems have been proposed which include those of the type in which the volume of ultrafiltrate removed is determined by indirect measurements such as rate of removal of ultrafiltrate or weight of the ultrafiltrate removed. Such systems inherently are inaccurate because they are using surrogates to determine volume. In such systems, there shall always be an error within the volume determination because the measurements are not directly on volume itself. The error that occurs may be small and insignificant when treating patients of an adult size. However, when these errors are scaled down and the patient is a 3 kilogram infant, the errors become significant, causing the patient to be thermodynamically unstable CVVH has also been used in combination with other extracorporeal therapies, including ECMO. In that configuration, a single roller pump drives simultaneously the blood in the ECMO and CVVH circuits. Blood from the oxygenator is drained to the hemofilter and returns to the ECMO circuit via the ECMO bladder. A recent study reported that percent fluid overload was correlated with mortality in patients receiving CVVH. In another case report, the benefits of a combined ECMO-CVVH therapy were assessed to treat neonatal cardiac and respiratory failure. The results demonstrated that the reduction of fluid overload via CVVH could lead to a significant improvement in both oxygenation and cardiac output. Finally, similar benefits were observed when implementing CVVH along with ECMO in the pediatric intensive care unit. Those results suggest that the use of CVVH during ECMO is associated with improved fluid balance and caloric intake with less use of diuretics compared to standard ECMO approaches.

Significant issues associated with the implementation of this combined therapy are the complexity, cost, staffing requirements, and increased risk to an already complicated and expensive ECMO course of action. Although devices such as the Diapact (B. Braun Medical Inc., Bethlehem, Pa.) and the Prisma (Gambro Dasco S.p. A., Medolla, Italy) are commercially available and use a weight-based method of ensuring accuracy, no commercially available CRRT device is specifically approved for use in conjunction with ECMO.

Additionally, the Diapact's use is limited in neonatal and pediatric patients because the lowest ultrafiltration rate is 300 ml/hour and many patients in pediatric care require less than that. There is a need for a simplified ECMO-CVVH setup which may solve these and the many other potential problems associated with current ECMO-CVVH systems.

When using ECMO-CCVH systems, close attention is required to assess patient level of hydration as some inaccuracy in pump delivery of replacement fluid volume and pump extraction of ultrafiltrate fluid volume can occur, creating the potential for excessive fluid removal. Clinical experience has suggested that significant differences between set and observed fluid removal rates can occur, leading to cases of dehydration out of proportion to desired rates. Preliminary observations suggested that this difference might be due to replacement fluid pump inaccuracy of up to 12.5%. This inaccuracy has discouraged some ECMO physicians from using this potentially beneficial technique due to the lack of a simple and accurate intravenous fluid pump system capable of working against high flow rates seen in patients on ECMO. There is a need for an ECMO-CVVH system that also solves these problems.

Many patients not receiving ECMO also require renal replacement therapy in the intensive care unit while they are ill. CVVH is a common method of providing renal replacement therapy to critically ill and hemodynamically unstable patients in the pediatric intensive care unit. There is currently no FDA approved CVVH device for use in the neonatal and pediatric populations. Currently, because there is no other available choice approved for pediatrics and the fact that untreated renal failure can lead to death, physicians may resort to utilizing CVVH devices approved for adults to treat children. However, when adult approved CVVH devices are used on smaller patients, similar inaccuracy in fluid management as described above occur and complications are common.

There exists a need for systems and methods for fluid management for accurate continuous venovenous hemofiltration, which in some instances is combined and integrated with extracorporeal membrane oxygenation. In prior art systems in which a fluid management system is integrated with an ECMO system, as illustrated in FIG. 1, blood is filtered via a hemofilter 120 and the ultrafiltrate 125 is extracted from the hemofilter 120 via a first pump 130. Simultaneously, a second pump 135 delivers some replacement fluid 140 back into the filtered blood within the bladder 105. The main disadvantage of the combined system illustrated in FIG. 1 is the large pressure under which the ECMO circuit operates. The use of IV pumps 130, 135 to deliver or extract high flow rates of fluids under a pressure much higher than in the human body is controversial. The accuracy of a typical IV pump was tested in terms of the error between the programmed flow rate and the actual flow rate delivered by the pump for a range of pressures between 120 and 180 mmHg. The experiments that were repeated at three different flow rates (i.e., 1 L/hour, 500 mL/hour and 300 mL/hour) revealed an error increasing as a function of pressure and as a function of flow rate, illustrated in FIG. 2. Therefore, operating the two IV pumps of the CVVH circuit under the typical pressure of the ECMO circuit could lead to an increased ultrafiltrate removal from the patient and decreased fluid replacement to the patient. This phenomenon that has been observed to be more significant in smaller patients could result in rapid dehydration and could ultimately lead to shock. There is a need for a combined CVVH and ECMO system that solves this problem.

There also exists a need for a stand alone CVVH system designed specifically to provide accurate fluid management therapy across the range of size and weight seen from infancy to adulthood. There exists a need for systems and methods for fluid management capable of producing either perfect or negative fluid balance between ultrafiltrate removal and replacement fluid delivery. There also exists a need for systems and methods for fluid management capable of achieving electrolyte replacement over a range of flow rates needed to care for patients ranging from neonates to adults. Finally, there exists a need for systems and methods for fluid management that preserves patient safety, maintains sterility, is easy to operate, and is compact enough to fit near a patient's bed.

SUMMARY OF THE INVENTION

The present invention is an accurate continuous venovenous hemofiltration (CVVH) fluid management system that is configured for operation as a stand alone unit and for integration with an ECMO circuit. It is an objective of the CVVH system to produce either a zero or negative fluid balance between the replacement fluid delivered to the patient and the ultrafiltrate extracted from the hemofilter. The present invention also discloses a method for managing fluid for accurate continuous venovenous hemofiltration, comprising the steps of filling a first container with replacement fluid; continuously filtering unfiltered blood to extract ultrafiltrate; transferring the replacement fluid from the first container to the filtered blood; occurring simultaneously with the performance of the previous step, transferring the ultrafiltrate to a second container in an amount equal to the amount of replacement fluid transferred from the first container; continuously monitoring the state of replacement fluid in the first container and the state of ultrafiltrate in the second container; upon detecting that the first container no longer contains replacement fluid, stopping the transfer of ultrafiltrate to the second container; after transferring all of the replacement fluid from the first container, refilling the first container with additional replacement fluid; and occurring simultaneously with the performance of the previous step, emptying the ultrafiltrate that is in the second container so that the second container no longer contains ultrafiltrate.

A method of the present invention further comprises the step of repeating the foregoing steps to achieve a zero fluid balance between the ultrafiltrate extracted from the filtered blood and the replacement fluid transferred to the filtered blood.

To achieve a negative fluid balance between the ultrafiltrate extracted from the filtered blood and the replacement fluid transferred to the filtered blood, the method of the present invention further comprises the steps of transferring a portion of the replacement fluid to a third container so that the portion of replacement fluid transferred to the third container is not combined with the filtered blood and emptying the portion of the replacement fluid that is in the third container so that the third container no longer contains replacement fluid.

In addition, a method of the present invention may also comprise the step of continuously monitoring a patient to determine the need for zero fluid balance and negative fluid balance.

The present invention also discloses a system for managing fluid for accurate continuous venovenous hemofiltration, comprising a hemofilter continuously filtering unfiltered blood to extract ultrafiltrate; a first container filled with replacement fluid, wherein the replacement fluid is transferred from the container to the filtered blood; a second container and the first container coupled to a translating arm, wherein the translating arm moves to simultaneously allow the replacement fluid to be transferred from the first container to the filtered blood and allow the ultrafiltrate to be transferred from the hemofilter to the second container, the amount of the replacement fluid and the ultrafiltrate transferred being equal to each other; at least one sensor being structurally connected to the translating arm to continuously monitor the relative position of the translating arm, thereby determining whether there is replacement fluid contained in the first container and ultrafiltrate contained in the second container; upon at least one sensor detecting that the translating arm is in a minimum or a maximum position in connection with the first container and the second container, means for causing the translating arm to stop and reverse its direction, wherein, in a first phase, the first container is refilled with additional replacement fluid at the same time as the ultrafiltrate is emptied from the second container, or wherein, in a second phase, the replacement fluid is transferred from the first container at the same time as the ultrafiltrate is extracted from the hemofilter and transferred to the second container. The foregoing system allows one to achieve a zero fluid balance between the ultrafiltrate extracted from the filtered blood and the replacement fluid transferred to the filtered blood.

The present invention discloses a system further comprising a third container for containing a portion of the replacement fluid that is being transferred from the first container to the filtered blood so that the portion of replacement fluid transferred to the third container is not combined with the filtered blood, thereby producing a negative fluid balance between the ultrafiltrate extracted from the filtered blood and the replacement fluid transferred to the filtered blood.

The aforementioned system achieves a perfect fluid balance. However, to achieve a net negative fluid balance, a singular piston-syringe is needed. This piston-syringe is connected to the replacement fluid piston-syringe to extract a portion of the replacement fluid to achieve a net negative fluid balance.

BRIEF DESCRIPTION OF THE DRAWINGS

Non-limiting and non-exhaustive embodiments are described with reference to the following figures, wherein like reference numerals refer to like parts throughout the various views unless otherwise specified.

FIGS. 4A and 4B are drawings depicting the principles of conservation of volume in fluid management as applied according to the present invention;

DETAILED DESCRIPTION OF A PREFERRED EMBODIMENT

Various embodiments are described more fully below with reference to the accompanying drawings, which form a part hereof, and which show specific embodiments of the invention. However, embodiments may be implemented in many different forms and should not be construed as limited to the embodiments set forth herein; rather, these embodiments are provided so that this disclosure will be thorough and complete, and will fully convey the scope of the invention to those skilled in the art. Accordingly, the following detailed description is, therefore, not to be taken in a limiting sense.

Figure 1:
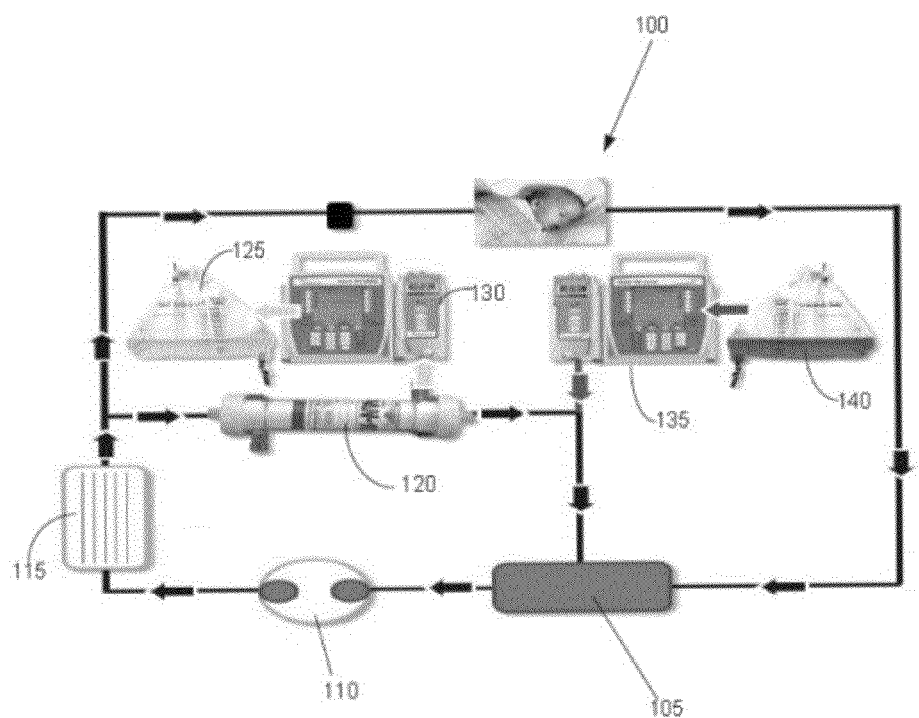
FIG. 1 is a schematic representation of a prior art ECMO-CVVH system.
Figure 2:
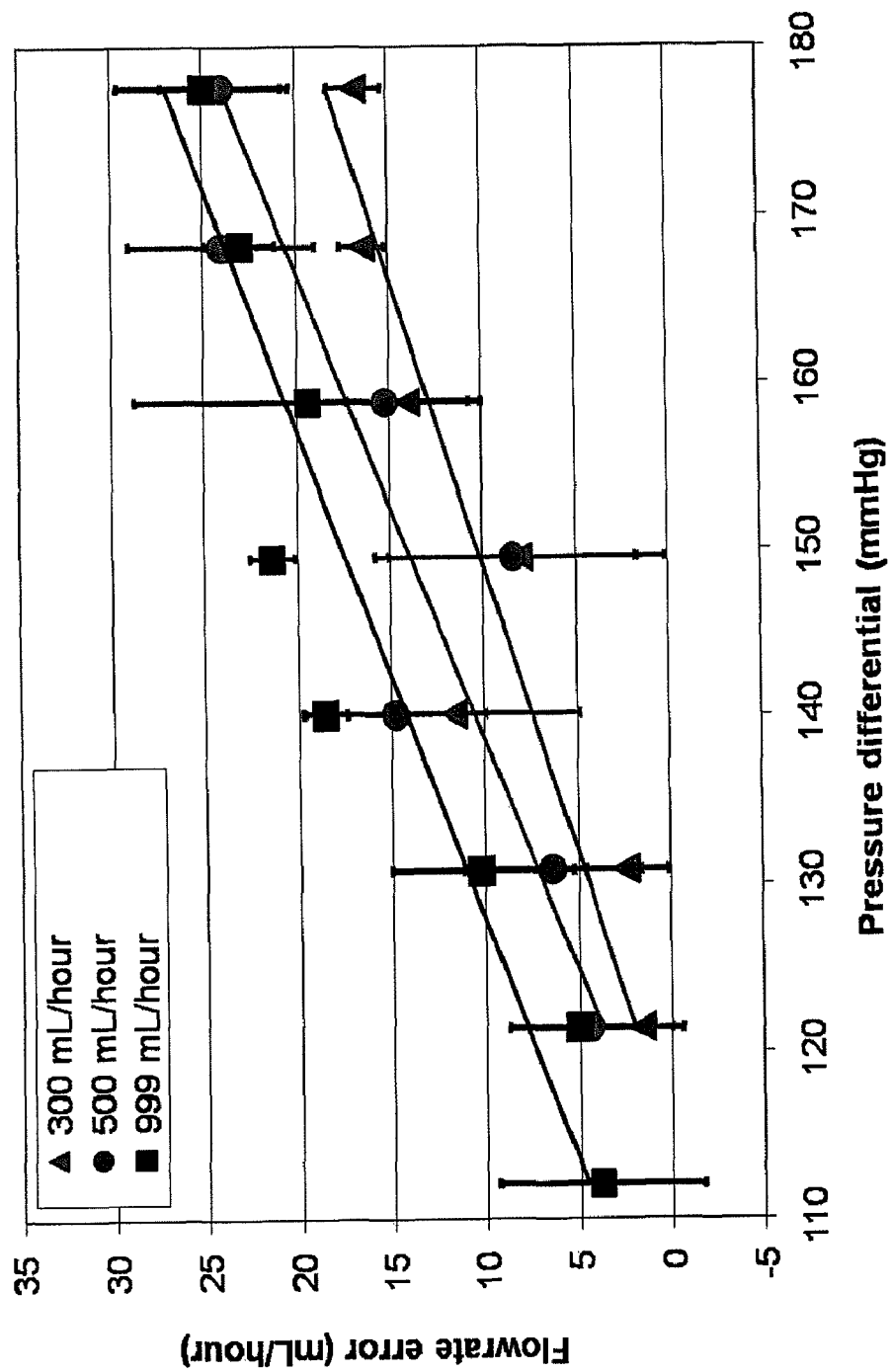
FIG. 2 is a graphical representation of IV pump accuracy measurements, namely showing flow rate error as a function of pressure differential applied across an IV pump.
Figure 3A:
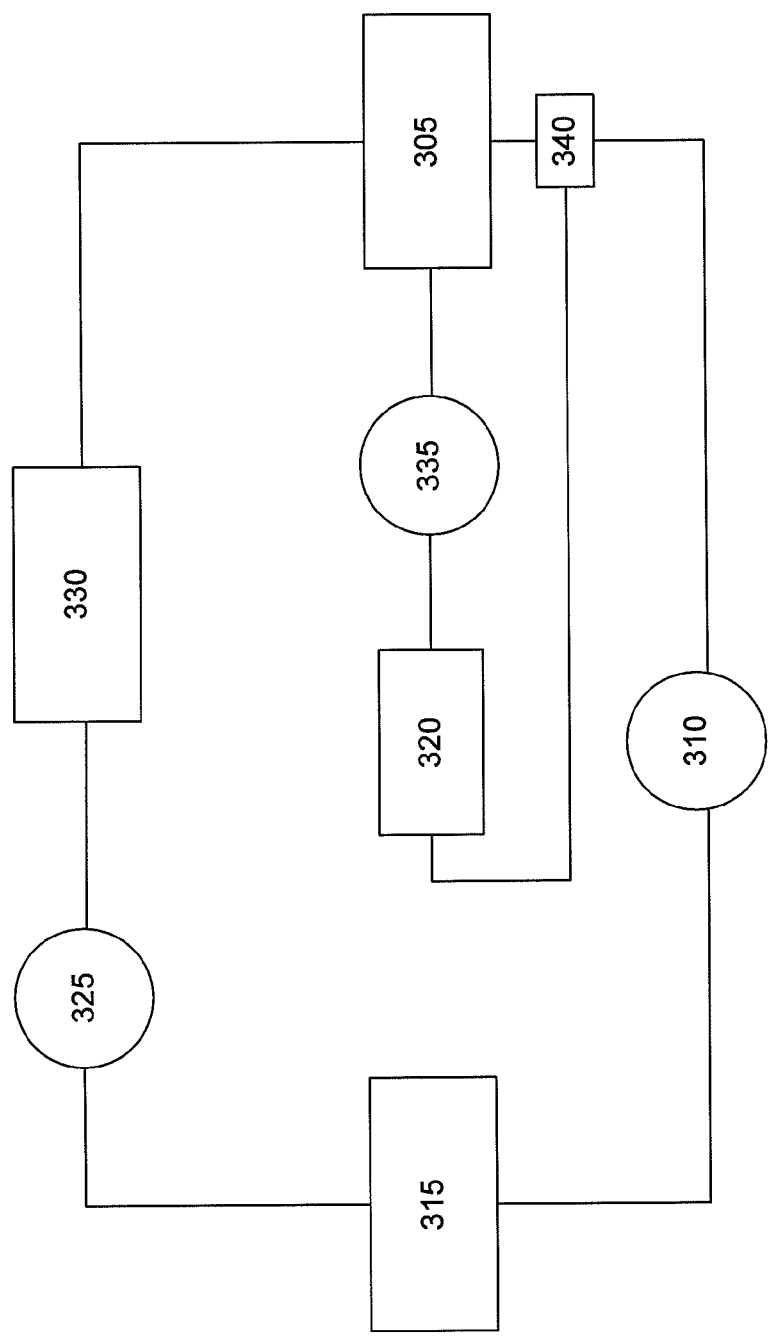
FIGS. 3A and 3B are schematic representations of ECMO-CVVH systems of the present invention.

Referring now to FIG. 3A, the present invention is a combined ECMO-CVVH system 300 comprised of an ECMO bladder 305, a blood pump 310, an oxygenator 315, and a flow probe 325. Blood is continuously drained from a patient's venous system and circulated through the ECMO bladder 305. The blood pump 310 draws blood from the ECMO bladder 305, which works like the right atrium. The function of this ECMO bladder 305 is to prevent negative pressure from pulling the vessel wall into the cannula and to reduce the risk of damage to the vena cava. The blood pump 310 serves as an artificial heart that drives the blood simultaneously through the entire combined ECMO-CVVH system 300. The blood is carried through the oxygenator 315, which serves as an artificial lung that oxygenates the blood and removes carbon dioxide. Once the blood has been oxygenated, pump 310 causes the oxygenated blood to be carried into the patient. The flow probe 325 is used to physically test the amount of fluid that is running in the circuit. The output of the flow probe 325 is a number representative of the amount of fluid running in the circuit, measured in liters per hour.

As illustrated in FIG. 3A, the CVVH device 320 is inserted between the blood pump 310 and the oxygenator 315. The blood pump 310 drives the deoxygenated blood through the CVVH device 320. The novel CVVH device 320, described in greater detail below in connection with FIGS. 4A-9B, is configured to directly measure the volume of fluid removed from a patient during therapy and utilize that measurement in order to determine a more accurate amount of replacement fluid that is to be returned to the patient. This aspect of the present invention may be utilized in a stand alone CVVH device or within the CVVH portion of the combined ECMO-CVVH system 300. There is a direct correlation between the amount of volume that is extracted from a patient in ultra filtrate that is created during therapy and the amount that optimally should be returned to the patient as replacement fluid. The novel aspect of the CVVH portion of the present invention facilitates optimal return of replacement fluid. After the blood has been processed in the CVVH device 320, it is carried back to the ECMO bladder 305. The blood is then circulated back through the ECMO system to the patient. Prior to the filtered blood entering the patient, the flow probe 325 measures the actual post-membrane flow for calculation of the hemofilter runoff.

Figure 3B:
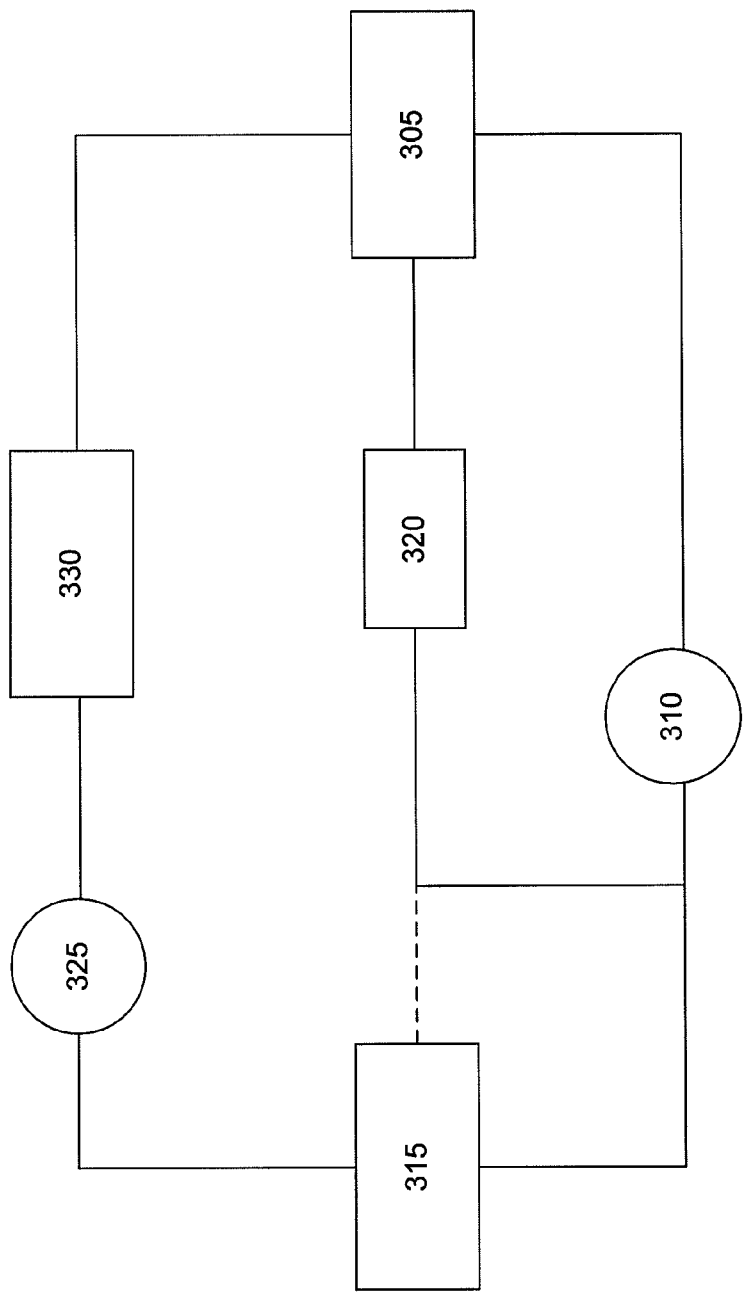

FIG. 3B illustrates an alternative embodiment of the present invention, a combined ECMO-CVVH system 300 comprised of an ECMO bladder 305, an ECMO blood pump 310, an oxygenator 315, a flow probe 325, a novel CVVH device 320, a CVVH blood pump 335, and a post bladder blood access port 340. Blood is continuously drained from a patient's venous system and circulated through the ECMO bladder 305. The ECMO blood pump 310 draws blood from the ECMO bladder 305, which works like the right atrium. The function of this ECMO bladder 305 is to prevent negative pressure from pulling the vessel wall into the cannula and to reduce the risk of damage to the vena cava. The ECMO blood pump 310 serves as an artificial heart that drives the blood through the ECMO circuit 300 and back to the patient. The blood is carried through the oxygenator 315, which serves as an artificial lung that oxygenates the blood and removes carbon dioxide. Once the blood has been oxygenated, the ECMO blood pump 310 causes the oxygenated blood to be carried into the patient.

As illustrated in FIG. 3B, in this embodiment, the CVVH device 320 is inserted between the ECMO blood pump 310 and the ECMO bladder 305. In this configuration a CVVH blood pump 335 drives deoxygenated blood from the ECMO bladder 305 through the CVVH device 320 rather than relying on the ECMO blood pump 310 to drive the blood. The novel CVVH device 320 will be described in greater detail below in connection with FIGS. 4A-9B. After the blood has been processed in the CVVH device 320, it is carried back to post bladder blood access port 340. The blood then continues through the ECMO system to the patient. Prior to the filtered blood entering the patient, the flow probe 325 measures the actual post-membrane flow for calculation of the hemofilter runoff.

Referring to FIGS. 4A and 4B, aspects of CVVH system 400 illustrating the principles of "conservation of volume" in fluid management as applied in the present invention are shown. As, illustrated, a unique linear positioner 402 is employed as shown in FIGS. 4A and 4B. The linear positioner 402 translates within a cylinder 405 and simultaneously controls both the delivery of replacement fluid 410 from a replacement fluid bag 411 and the removal of ultrafiltrate 415 after the blood has been filtered by a hemofilter 416. The linear positioner 402 divides the cylinder 405 into two chambers, namely replacement fluid chamber 420 and ultrafiltrate fluid chamber 425. The replacement fluid chamber 420 is dedicated to the delivery of replacement fluid 410 and the ultrafiltrate fluid chamber 425 is dedicated to the drainage of ultrafiltrate 415. The linear positioner 402, which is commercially available, facilitates balanced removal of ultrafiltrate and delivery of replacement fluids. In the present embodiment, linear positioner 402, model number LP28-T0150-D01-G21-M1322-H3-L2, is manufactured by Parker Hannifin Corporation of Cleveland Ohio. It is contemplated that other linear positioners may be utilized so long as they perform the function of operating both the replacement fluid and ultrafiltration piston-syringes. The pinch valves utilized in the present embodiment are also commercially available, model number 100P3-MP12-05-S-F, manufactured by Bio Chem Valve Inc, of Boonton, N.J. It is contemplated that other pinch valves or valve systems may be used.

A syringe-pump system 430 consisting of a syringe 431 and piston 432, a negative fluid balance bag 435, and valves 470 and 475 are located downstream of the replacement fluid chamber 420. The syringe-pump system 430 removes some replacement fluid 410 before its delivery to an ECMO bladder in order to achieve a net negative fluid balance. When the syringe 431 is full, its contents are emptied into the negative fluid balance bag 435. The syringe pump system 430 utilized in the present embodiment of the invention is commercially available, model 309653, manufactured by Becton Dickinson of Franklin Lakes, N.J. It is contemplated that syringes other than the specific model identified herein may be utilized, so long as they perform the function of facilitating a negative fluid balance within the system.

There are two consecutive steps involved in the operation of this aspect of the CVVH system illustrated. Switching between the first and second steps is controlled by a system of valves, which allow or block communication between the various components of the fluid management system. Valves 450, 455, 460, 465, 470, and 475 are used to control the flow of filtered blood and replacement fluid in the system. Valve 450 is positioned between the fluid replacement bag 411 and the replacement fluid chamber 420. Valve 455 is positioned between the replacement fluid chamber 420 and the filtered blood. Valve 460 is positioned between the hemofilter 416 and the ultrafiltrate fluid chamber 425. Valve 465 is positioned between the ultrafiltrate fluid chamber 425 and the drainage bag 445. Valve 470 is positioned downstream between the filtered blood and the syringe 431 and valve 475 is positioned between the negative balance bag 435 and the syringe 431.

Referring now to FIG. 4A, in the first step, the linear piston 400 moves up within the cylinder 405. Accordingly, valve 460 is open and valve 465 is closed, thereby allowing ultrafiltrate 415 to enter and fill the ultrafiltrate fluid chamber 425. Concurrently, valve 450 is closed and valve 455 is open, thereby allowing replacement fluid 410 to exit the replacement fluid chamber 420.

In this first step, the same volumes of ultrafiltrate 415 and replacement fluid 410 are extracted and delivered, respectively. In the event that it is determined that a patient has fluid overload, the system may be configured to generate a net negative fluid balance in order to correct the fluid overload. A net negative fluid balance is achieved using the syringe pump system 430 located downstream of the replacement fluid chamber 420. In this case, valve 470 is open and valve 475 is closed, thereby allowing a portion of the replacement fluid to be captured in the syringe 431 of the syringe-pump system 430. Hence, the captured portion of replacement fluid will not enter the ECMO bladder. For example, during operation, if 500 ml of ultrafiltrate 415 is removed from the patient, the system automatically pulls up 500 ml of replacement fluid from the replacement fluid bag 411. If the 500 ml of replacement fluid is pushed back into the patient, there would be an even balance. To create a negative balance, downstream of the pump, valve 470 is opened so that replacement fluid 410 may be extracted and placed in the negative fluid balance bag 435. In this example, the amount of replacement fluid that is delivered back to the ECMO bladder is less than 500 ml.

It is also contemplated that the present invention shall include a processor, and a software module that operatively controls the motion of the syringe pump system 430 and the linear positioner 402. The linear positioner 402 controls the replacement fluid piston-syringe and the ultrafiltration piston-syringe and thereby controls the rate of fluid replacement and extraction with respect to each other. When it is necessary to create the negative fluid balance, the syringe pump system 430 is automatically engaged by the processor and software controls to facilitate an appropriate level of replacement fluid removal from the circuit. The processor and software module shall be completely integrated and are operatively connected to a user interface that allows a system user to input data representative of the rate at which fluid is to be replaced and the rate at which fluid is to be extracted from a patient.

Now turning to FIG. 4B, in the second step, the linear piston 400 moves down within the cylinder 405. Accordingly, valve 460 is closed and valve 465 is open, thereby allowing ultrafiltrate 415 to drain from the ultrafiltrate fluid chamber 425 into the drain bag 445. Concurrently, valve 450 is open and valve 455 is closed, thereby allowing replacement fluid 410 from the replacement fluid bag 411 to enter and fill the replacement fluid chamber 420. If the syringe pump system 430 was used to produce a net negative fluid balance as described in the first step in connection with FIG. 4A, then the syringe 431 that contains replacement fluid drains into the negative balance bag 435 and the contents of the negative balance bag 435 are emptied. To allow this process to occur, valve 470 is closed and valve 475 is open.

Figure 5A:
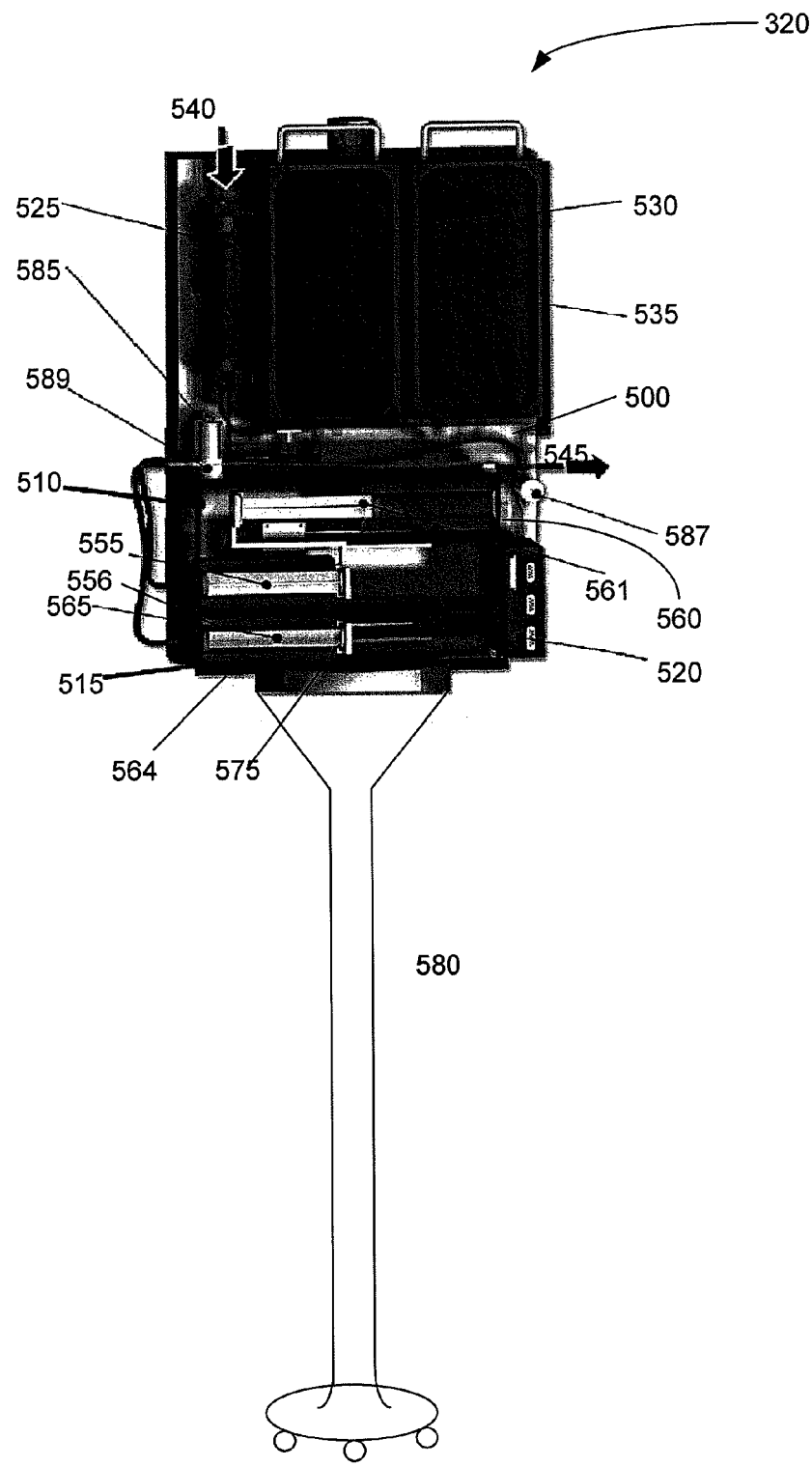
FIGS. 5A and 5B are drawings showing the front and back views, respectively, of a novel CVVH or fluid management device.
Figure 5B:
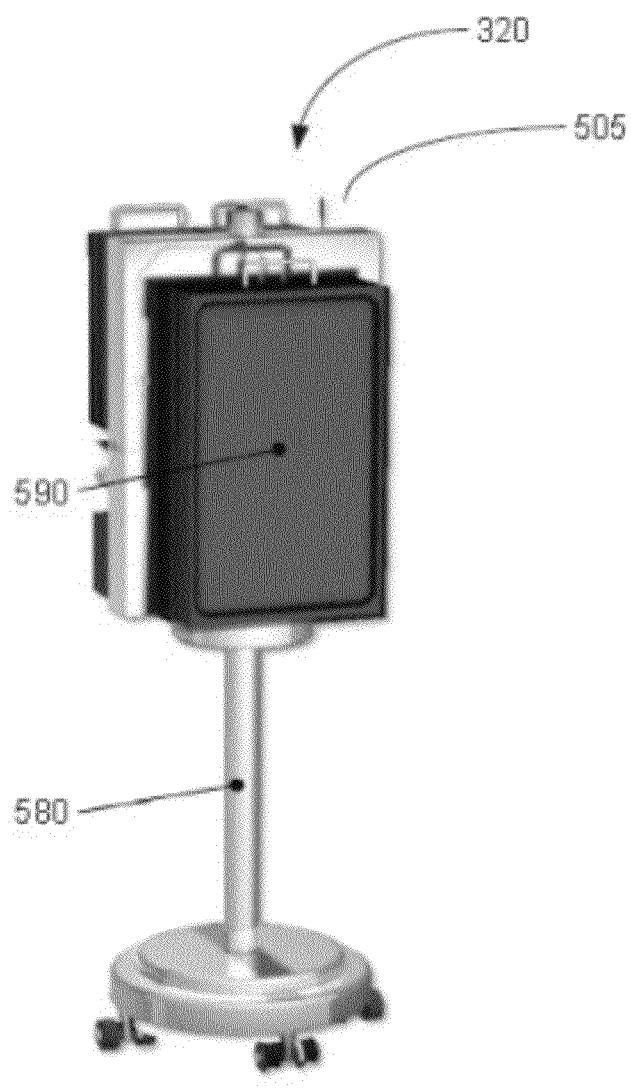

One embodiment of the present invention as described above in FIGS. 4A and 4B is illustrated herein in connection with FIGS. 5A and 5B. In an effort to present a compact design, the mechanical implementation of the above-described principles is modified such that a dual syringe-pump system that includes a pair of pistons coupled to a translating arm is used to create two separate chambers instead of the linear piston 400 illustrated in FIGS. 4A and 4B. This aspect of the present invention is described in greater detail herein below.

Referring now to FIGS. 5A and 5B, the front and back views, respectively, of a novel CVVH device are shown. The CVVH device 320 has a front panel 500 as shown in FIG. 5A and a back panel 505 as shown in FIG. 5B.

In FIG. 5A, the front panel 500 includes a perfect fluid balance pump compartment 510, a negative fluid balance pump compartment 515, a stepper drive 520, a hemofilter 525, a replacement fluid bag 530 and a negative fluid balance bag 535. An inlet 540 is connected to the membrane oxygenator 315 of the ECMO system of FIG. 3 while an outlet 545 is connected to the ECMO bladder 305 of FIG. 3. The CVVH device 320 can be mounted on a stand 580 with wheels for mobility. Stepper drive 520 is commercially available, manufactured by Parker Hannifin, model number VIX-250. It is contemplated that stepper drives other than the specific model identified herein may be utilized, so long as it performs the function of controlling the motion of the linear positioner.

Figure 6:
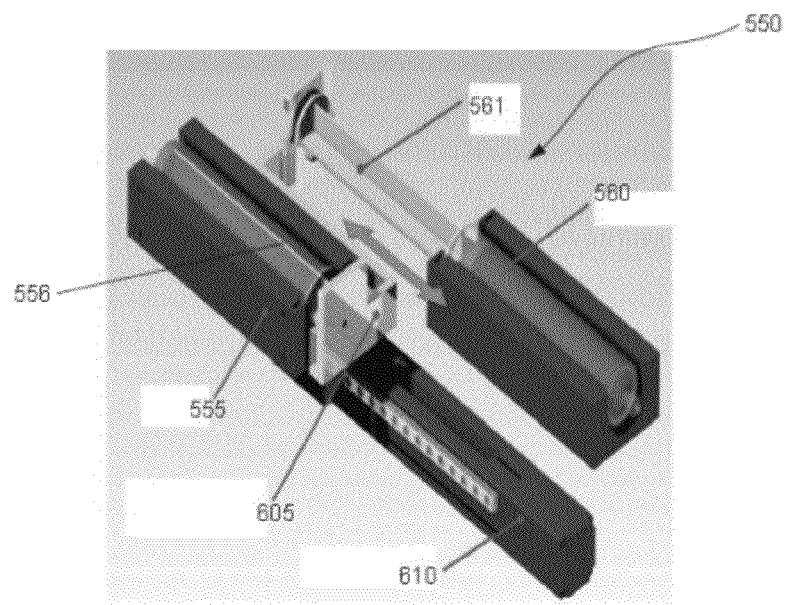
FIG. 6 is a drawing of a dual syringe-pump system with a pair of pistons coupled to a translating arm that may be used in an embodiment of the present invention.

Referring still to FIG. 5A, the perfect fluid balance pump compartment 510 houses a dual syringe-pump system 550, which includes a replacement fluid syringe 555, replacement fluid piston 556, a toxin clearance or ultrafiltration syringe 560, and toxin clearance or ultrafiltration piston 561. The pistons 556 and 561 are coupled to a translating arm 605, as shown in FIG. 6, which is a detailed illustration of the dual syringe-pump system 550. This syringe-pump system 550 is used to achieve a perfect fluid balance.

Turning briefly to FIG. 6, the dual syringe-pump system 550 incorporated in the present invention consists of a pair of pistons 556 and 561 coupled to a single translating arm 605. The pistons 556 and 561 push or pull fluid in their respective syringes 555 and 560 (60 cc syringe model 309653, BD, Franklin Lakes, N.J.). Syringe 555 delivers replacement fluid while syringe 560 extracts the ultrafiltrate.

This dual syringe-pump system 550 achieves a perfect fluid balance as the displacement of the translating arm 605 is identical for each piston while maintaining sterility as the replacement fluid and ultrafiltrate are stored in their respective syringes 555 and 560. The translating arm 605 is attached to a bearing truck (not shown) driven by a linear positioner 610 (LP28T0150-D01-G21-M1322-H3-L2, Parker Hannifin Corp., Cleveland, Ohio). The linear positioner 610 consists of a lead screw (not shown) and a stepper motor (not shown) programmed via a stepper drive 520 (FIG. 5A) mounted on the front panel 500. The linear positioner 610 utilized in the embodiment illustrated is dimensioned to achieve up to four strokes per minute, resulting in a maximum flow rate of 8 L/hour. It is contemplated that maximum allowable strokes per minute and thereby the maximum flow rate may be modified by altering the dimensions of the linear positioner 610.

Now turning back to FIG. 5A, the negative fluid balance pump compartment 515 houses a singular syringe-pump system 564 having a negative fluid balance syringe 565 and a negative fluid balance piston 575. This singular syringe-pump system 564 extracts a portion of the replacement fluid in order to achieve a net negative fluid balance. The singular syringe-pump system 564 is mounted in-line with the dual syringe-pump system 550. The system 564 extracts replacement fluid before this fluid is delivered to the patient, thus reducing the overall replacement fluid flow rate while maintaining the same ultrafiltrate removal flow rate.

Figure 7:
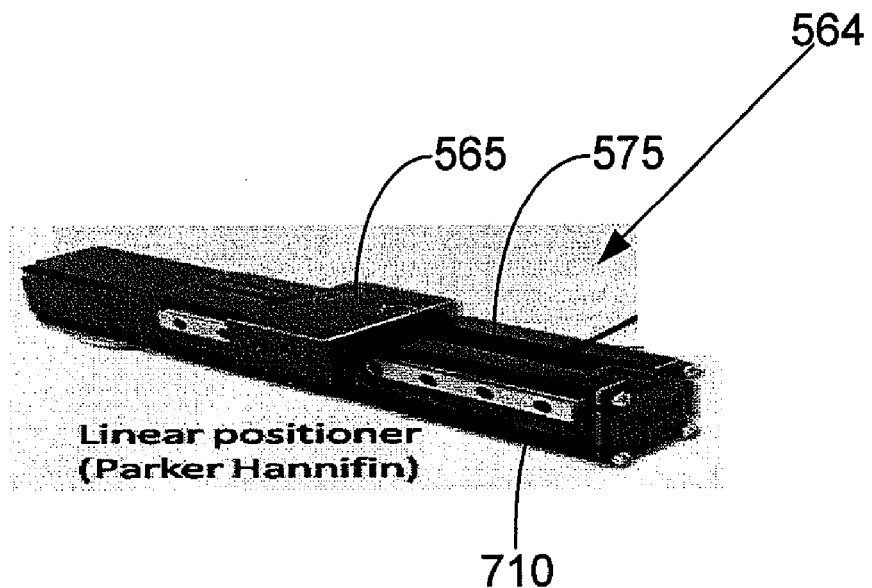
FIG. 7 is a drawing of a singular syringe-pump system with a single piston that may be used in an embodiment of the present invention.

Briefly turning to FIG. 7, the singular syringe-pump system 564 used in the present invention is shown. As mentioned previously, the system 564 has a negative fluid balance syringe 565 and a negative fluid balance piston 575. Similar to the dual piston-syringe system 550 of FIG. 6, this singular piston-syringe system 564 is driven by a linear positioner 710 that consists of an identical lead screw (not shown) and stepper motor (not shown) programmed via a stepper drive 520 (FIG. 5A) mounted on the front panel 500. Specifically, the stepper drive 520 controls the motion of both piston-syringe systems 550 and 564.

Referring back to FIG. 5A, the compartments 510 and 515 can be enclosed in a transparent box with a hinged lid made of polycarbonate in order to allow for easy access. In FIG. 5A, space is provided above the compartments 510 and 515 for the replacement fluid bag 530 and the negative fluid balance bag 535. These bags 530 and 535 can be placed in individual compartments as shown in FIG. 5A, whereby the compartments for the bags have a transparent box containing a sliding drawer that accommodates a 1000 mL disposable bag (Viaflex bag, Baxter International Inc., Deerfield, Ill.). The present invention was designed as described herein to simplify the handling of the fluids and to ensure fluid sterility, as well as the sterility of the whole system.

Before the CVVH or fluid management device 320 can function properly, a replacement fluid bag 530 filled with replacement fluid is positioned in the CVVH device 320 and an empty negative fluid bag 535 is positioned in the CVVH device 320. In addition, before the combined ECMO-CVVH system is connected to the patient, the replacement fluid syringe 555 is filled with replacement fluid while the ultrafiltration or toxin clearance syringe 560 is mounted with its piston 561 pushed to its lowest position (i.e., minimum stroke position).

In FIG. 5A, the hemofilter 525 can be mounted vertically on the left side of the replacement fluid bag 530. Other components of the front panel 500 include tubing (high-purity medical grade silicone tubing, part #51845K55, McMaster-Carr, Aurora, Ohio) for connecting the syringes and fluid bags to the stepper driver and three three-way pinch valves 585, 587, and 589 (100P3-MP12-05-S-F, Bio-Chem Valve Inc., Boonton, N.J.) for controlling the path of each fluid from the syringes 555, 560, and 565 to the tubing network. The pinch valves chosen are designed such that there is no contact between the valve components and the fluid, thereby facilitating system sterility.

In FIG. 5A, pinch valve 585 connects the replacement fluid syringe 555 to either the hemofilter outlet or the replacement fluid bag 530. Pinch valve 587 connects the ultrafiltration or toxin clearance syringe 560 and either the ultrafiltrate port of the hemofilter or the ultrafiltrate clearance bag 590 shown in FIG. 5B. Pinch valve 589 connects the negative fluid balance syringe 565 to either the tube connecting the replacement fluid syringe 555 to the hemofilter outlet or the negative fluid balance bag 535.

Now referring to FIG. 5B, the back panel 505 is designed to house the ultrafiltrate clearance bag 590. For ease and simplicity, the ultrafiltrate clearance bag 590 can be housed in a compartment having a drawer for the bag 590. In this example, a 5000 mL disposable bag can be used for the collection of ultrafiltrate that is removed from the hemofilter 525 of FIG. 5A.

There are two modes of operation in accordance with the present invention, namely the production of perfect fluid balance and the production of net negative fluid balance. The first mode involves the dual syringe-pump system and the second mode involves the singular syringe-pump system.

Figure 8A:
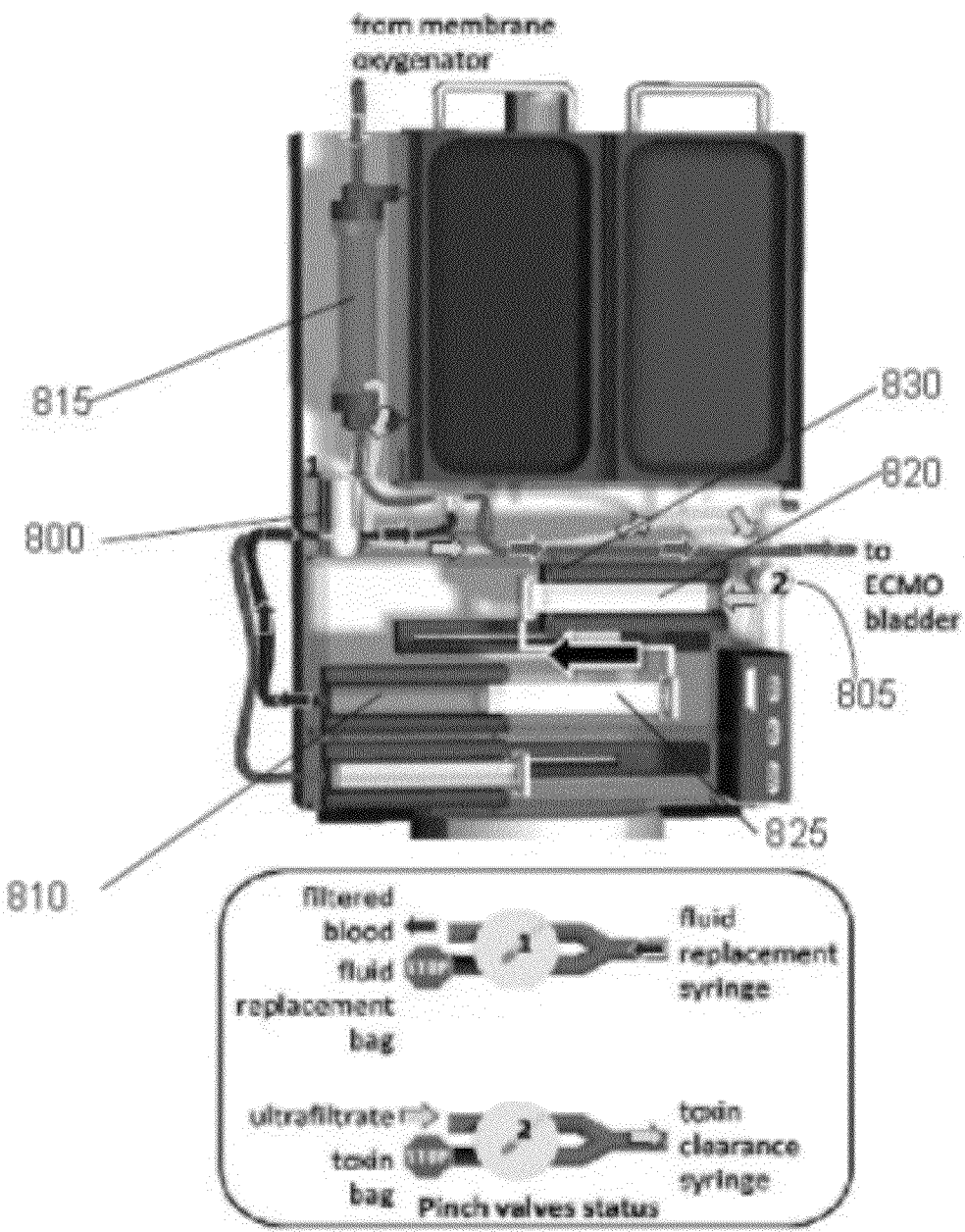
FIGS. 8A and 8B are drawings showing the mechanisms involved in the production of a perfect fluid balance according to the present invention.
Figure 8B:
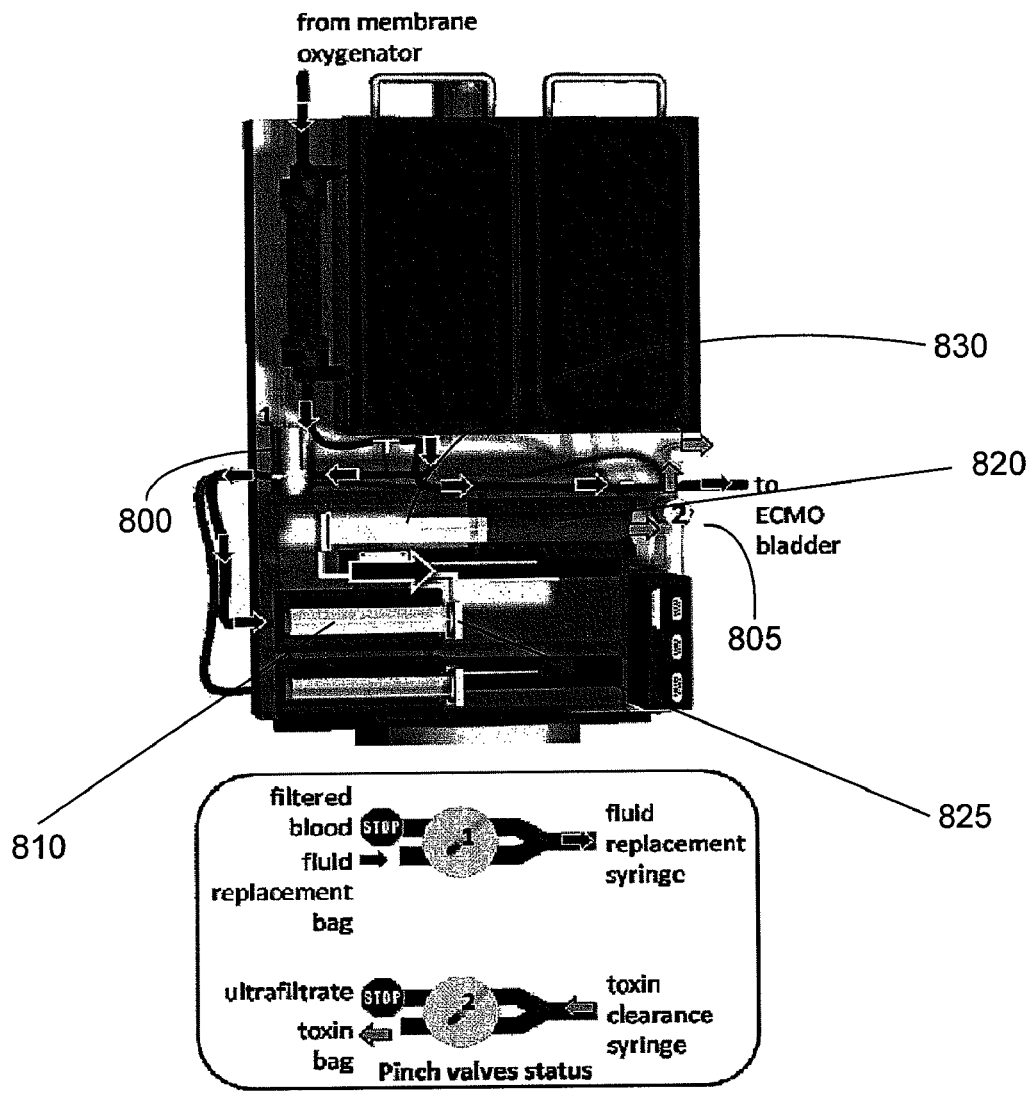

Now turning to FIGS. 8A and 8B, drawings showing the mechanisms involved in the production of a perfect fluid balance according to the present invention are illustrated. A perfect fluid balance is attained in two phases. FIG. 8A represents the first phase. In FIG. 8A, the first phase in the production of a perfect fluid balance consists of the delivery of replacement fluid and the extraction of ultrafiltrate. Two pinch valves 800 and 805 are involved in performing these functions. The first pinch valve 800 connects the replacement fluid syringe 810 to the filtered blood coming from the hemofilter 815. The second pinch valve 805 connects the ultrafiltrate coming from the hemofilter 815 to the ultrafiltration or toxin clearance syringe 820. During the first phase, while replacement fluid is delivered by the replacement fluid syringe 810 and is mixed with the blood filtered by the hemofilter 815, ultrafiltrate is extracted from the hemofilter 815 and is stored in the toxin clearance syringe 820. When the pistons 825 and 830 reach their maximum stroke, specifically when the replacement fluid syringe 810 is full and the ultrafiltration syringe 820 is empty, sensors mounted on the linear positioner relay this information to the pinch valves 800 and 805. In response to receiving this information, the pinch valves 800 and 805 switch to their opposite state and the linear positioner drives the pistons 825 and 830 in their opposite direction.

The sensors, mounted on the linear positioner, are utilized to transmit information reflecting the location of the linear positioner along the rail. There are at least two sensors, which, in the present embodiment indicate whether the linear positioner is at the beginning or at the end of the rail. These sensors interface with the pinch valves in the system. The sensors are used to switch the pinch valves to different configurations. Each time the linear positioner reaches the end of the rail, the pinch valves are switched to their opposite state. If a first pinch valve is open, the second pinch valve is closed and if the second pinch valve is open the first pinch valve is closed.

FIG. 8B represents the second phase. In FIG. 8B, the second phase in the production of a perfect fluid balance consists of refilling the replacement fluid syringe 810 and draining the ultrafiltration syringe 820. The first pinch valve 800 now connects the replacement fluid bag 840 to the replacement fluid syringe 810 and the second pinch valve 805 connects the ultrafiltration syringe 820 to the ultrafiltrate clearance bag located on the back panel (not shown) of the CVVH device. Under the action of the translating arm, the empty replacement fluid syringe 810 refills with replacement fluid while the full ultrafiltration syringe 820 empties its toxin content into the ultrafiltrate clearance bag located on the back panel (not shown) of the CVVH device. When the novel CVVH device is operated to achieve a perfect fluid balance, these two phases are all that is necessary to achieve that result. Once the two-phase cycle has ended, the system reinitializes to restart phase one.

Figure 9A:
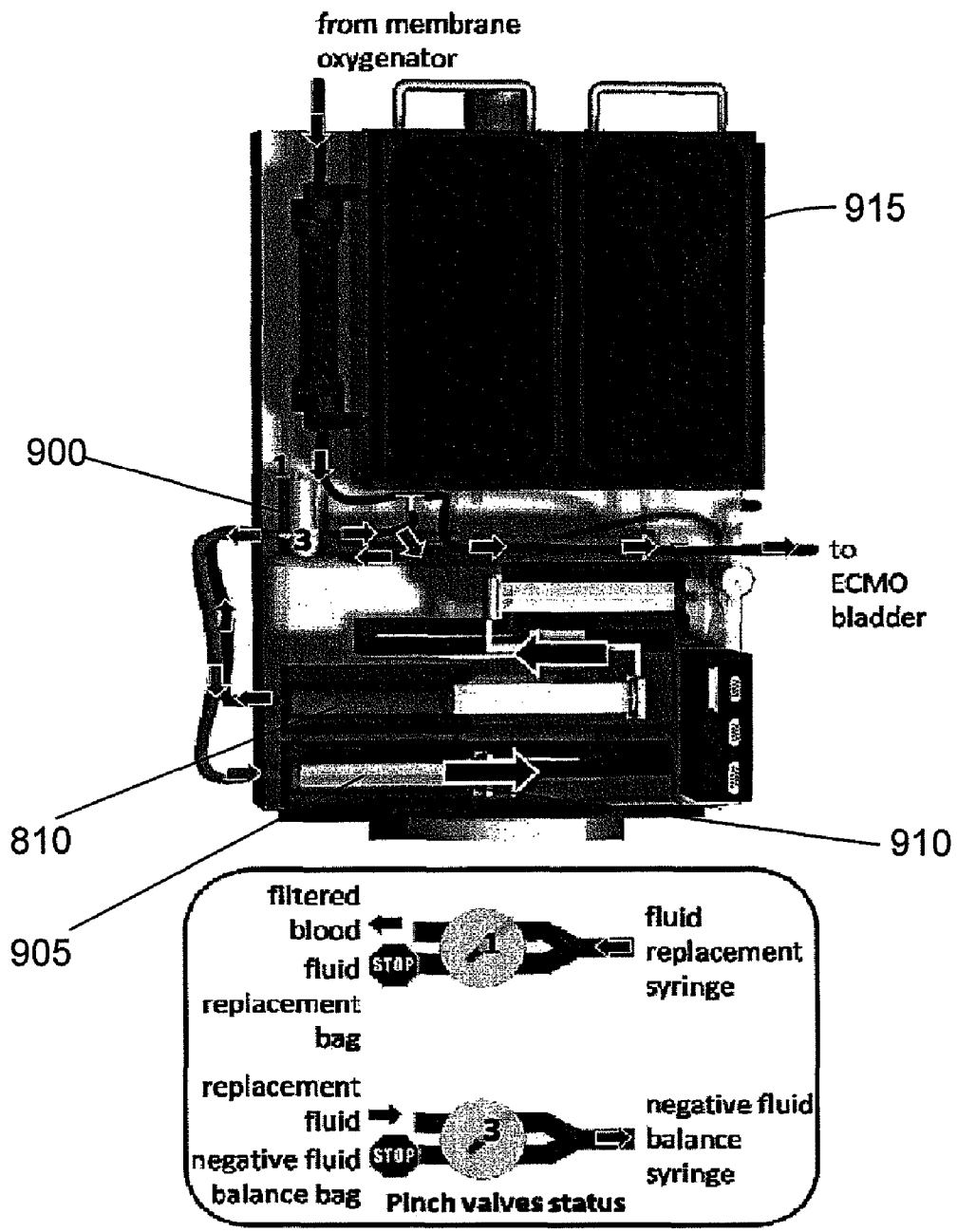
FIGS. 9A and 9B are drawings showing the mechanisms involved in the production of a negative fluid balance according to the present invention.
Figure 9B:
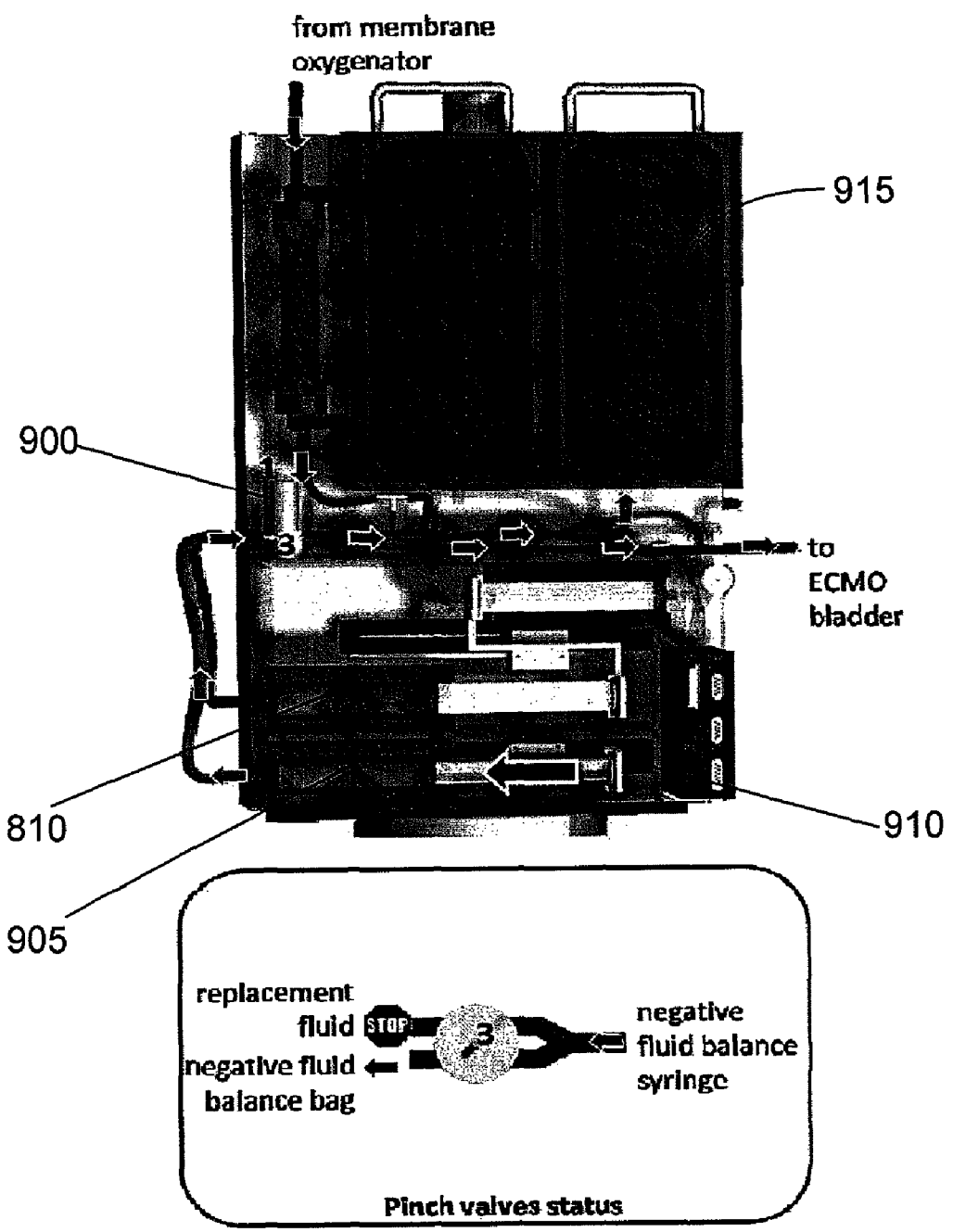

When the novel CVVH device is operated to produce a net negative fluid balance, two additional phases occur involving the singular syringe-pump system. FIGS. 9A and 9B are drawings showing the mechanisms involved in the production of a negative fluid balance according to the present invention. In FIG. 9A, the first phase occurs at the same time as the first phase in the production of a perfect fluid balance of FIG. 8A. In this phase, extra replacement fluid is removed and involves a third pinch valve 900 that connects the replacement fluid coming from the replacement fluid syringe 810 to the negative fluid balance syringe 905. While replacement fluid is delivered to the filtered blood by the replacement fluid syringe 810, some of the replacement fluid is captured by the negative fluid balance syringe 905 before this fluid gets injected into the filtered blood. The relative flow rates achieved by the replacement fluid syringe and the negative balance syringe determine the overall flow rate of fluid removal from the patient. When the negative fluid balance syringe 905 is full, the third pinch valve 900 switches to its opposite state and the piston 910 translates in the opposite direction as shown in FIG. 9B.

FIG. 9B represents the second phase. In FIG. 9B, the third pinch valve 900 allows communication between the negative fluid balance syringe 905 and the negative fluid balance bag 915. Once the negative fluid balance syringe 905 is full, the syringe 905 empties its contents into the negative fluid balance bag 915. As the piston 910 reaches its minimum stroke, pinch valve 900 switches back to its initial state and the cycle is repeated.

Figure 10:
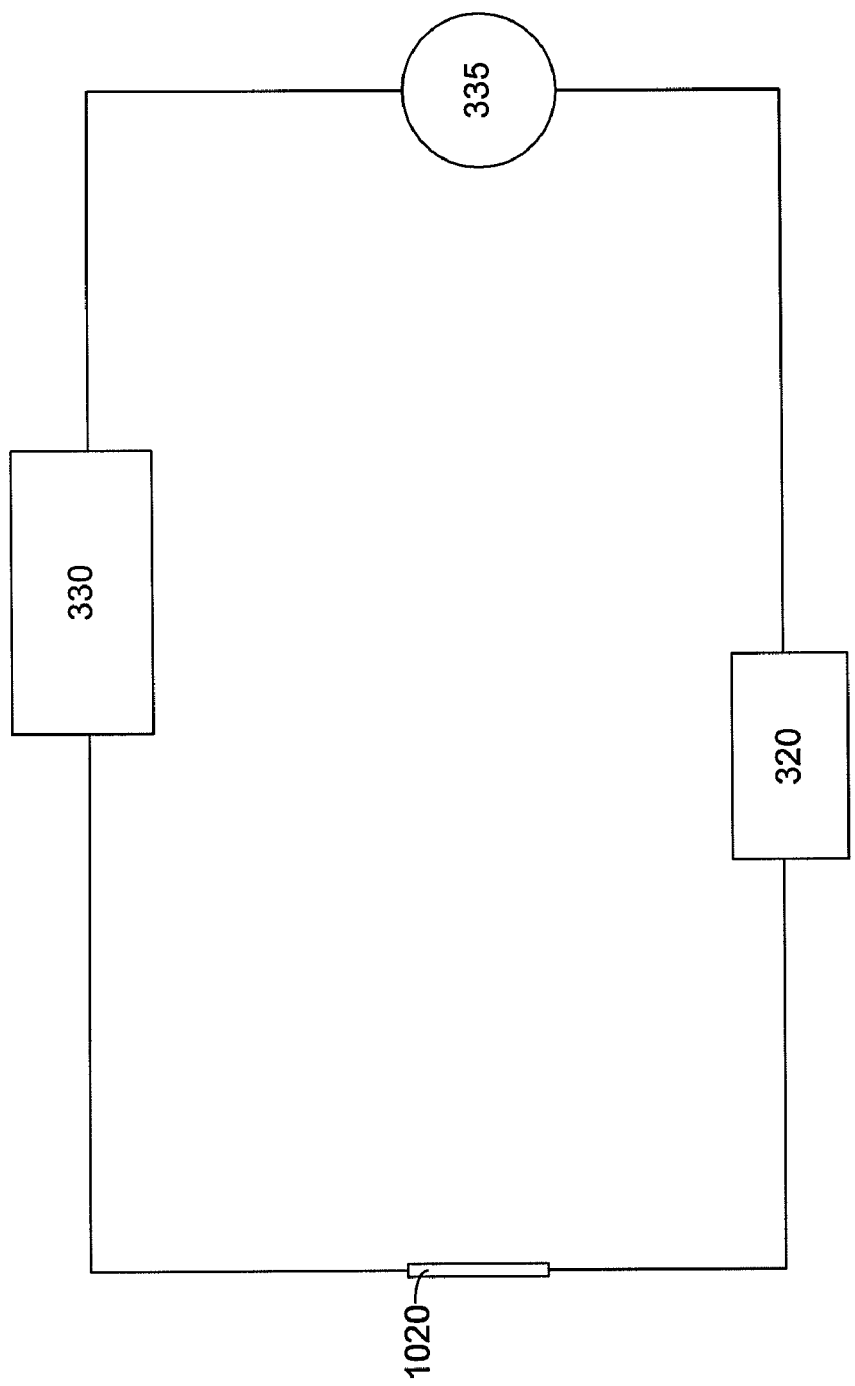
FIG. 10 is a schematic representation of stand alone CVVH system of the present invention.

Referring now to FIG. 10, the present invention is a CVVH system 336 for use in patients that are not receiving ECMO. The CVVH circuit utilizes the same components as previously described in FIG. 3B; however the method of obtaining venous blood from the patient differs. Since the patient is not on ECMO, central venous access must be obtained with the use of a multiple lumen large bore intravenous dialysis catheter (not shown) 336. Many standard dialysis catheters are commercially available (for example, the Mahurkar series —Model #539001 8F, 9 cm dual lumen dialysis catheter, Model #101001 12F, 13 cm triple lumen dialysis catheter, and Model #102003 12F, 20 cm triple lumen dialysis catheter, Tyco Healthcare, Mansfield Mass.) and the choice of catheter should be appropriate to the patient's size, expected duration of renal replacement therapy, and specific medical condition.

As illustrated in FIG. 10, the CVVH system 304 is comprised of a patient with a standard dialysis access catheter 1010, a CVVH blood pump 335, and the novel CVVH device 320. Using the CVVH blood pump 335, blood is continuously drained from a patient's venous system through the venous lumen of the dialysis catheter 336. The force generated by the CVVH blood pump 335 is utilized to circulate the blood through the novel CVVH device 320. In this configuration the novel CVVH device 320 is inserted in the venous lumen of the dialysis catheter 336 after the CVVH blood pump 335. Once the blood has been treated with CVVH device 320, it is returned into the arterial lumen of the dialysis catheter 336. The force generated by the CVVH blood pump 335 as well as the dual syringe pump system 550 subsequently returns the blood to the patient via the arterial lumen of the dialysis access catheter 336.

Reference may be made throughout this specification to "one embodiment," "an embodiment," "embodiments," "an aspect," or "aspects" meaning that a particular described feature, structure, or characteristic may be included in at least one embodiment of the present invention. Thus, usage of such phrases may refer to more than just one embodiment or aspect. In addition, the described features, structures, or characteristics may be combined in any suitable manner in one or more embodiments or aspects. Furthermore, reference to a single item may mean a single item or a plurality of items, just as reference to a plurality of items may mean a single item. Moreover, use of the term "and" when incorporated into a list is intended to imply that all the elements of the list, a single item of the list, or any combination of items in the list has been contemplated.

One skilled in the relevant art may recognize, however, that the invention may be practiced without one or more of the specific details, or with other methods, resources, materials, etc. In other instances, well known structures, resources, or operations have not been shown or described in detail merely to avoid obscuring aspects of the invention.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the claimed invention.

The above specification, examples and data provide a description of the manufacture and use of the invention. Since many embodiments of the invention can be made without departing from the spirit and scope of the invention, the invention resides in the claims hereinafter appended.

We claim:

1. A method for managing fluid for accurate continuous venovenous hemofiltration, comprising the steps of:
    (a) filling a first container with replacement fluid;
    (b) continuously filtering unfiltered blood to extract ultrafiltrate, thereby producing filtered blood;
    (c) transferring the replacement fluid from the first container to the filtered blood, thereby combining the replacement fluid with the filtered blood;
    (d) occurring simultaneously with the performance of step (c), transferring the ultrafiltrate to a second container in an amount equal to an amount of replacement fluid transferred from the first container;
    (e) continuously monitoring a state of the replacement fluid in the first container and a state of the ultrafiltrate in the second container;
    (f) upon detecting that the first container no longer contains the replacement fluid, stopping the transfer of the ultrafiltrate to the second container;
    (g) after transferring all of the replacement fluid from the first container, refilling the first container with additional replacement fluid; and
    (h) occurring simultaneously with the performance of step (g), emptying the ultrafiltrate that is in the second container so that the second container no longer contains the ultrafiltrate.

2. The method of claim 1, further comprising the step of: upon detecting that the second container no longer contains the ultrafiltrate, continuously repeating the steps (b) through (h) for producing zero fluid balance between the ultrafiltrate extracted from the filtered blood and the replacement fluid transferred to the filtered blood.

3. The method of claim 1, further comprising the steps of:
    (i) occurring simultaneously with the performance of the step (c), transferring a portion of the replacement fluid to a third container so that the portion of the replacement fluid transferred to the third container is not combined with the filtered blood, thereby producing a negative fluid balance between the ultrafiltrate extracted from the filtered blood and the replacement fluid transferred to the filtered blood; and
    (j) occurring simultaneously with the performance of the step (g), emptying the portion of the replacement fluid that is in the third container so that the third container no longer contains the replacement fluid.

4. The method of claim 3, further comprising the step of continuously repeating the steps (b) through (j).

5. The method of claim 1, further comprising the steps of:
    (i) continuously monitoring a patient to determine a need for a zero fluid balance and a negative fluid balance;
    (j) in the event that it is determined that the zero fluid balance is necessary, upon detecting that the second container no longer contains the ultrafiltrate, continuously repeating the steps (b) through (h) for producing the zero fluid balance between the ultrafiltrate extracted from the filtered blood and the replacement fluid transferred to the filtered blood; and
    (k) in the event that it is determined that the negative fluid balance is necessary,
        (1) occurring simultaneously with the performance of the step (c), transferring a portion of the replacement fluid to a third container so that the portion of the replacement fluid transferred to the third container is not combined with the filtered blood, thereby producing the negative fluid balance between the ultrafiltrate extracted from the filtered blood and the replacement fluid transferred to the filtered blood;
        (2) occurring simultaneously with the performance of the step (g), emptying the portion of the replacement fluid that is in the third container so that the third container no longer contains the replacement fluid; and
        (3) continuously repeating the steps (b) through (h) and (k).

6. A method for managing fluid for accurate continuous venovenous hemofiltration, comprising the steps of:
    (a) providing a specific amount of replacement fluid in a container;
    (b) providing a replacement fluid piston-syringe that is initially filled with the replacement fluid, whereas a piston of the replacement fluid piston-syringe is in a maximum stroke position;
    (c) providing an ultrafiltration piston-syringe that is initially empty, whereas a piston of the ultrafiltration piston-syringe is in a minimum stroke position;
    (d) coupling the replacement fluid piston-syringe and the ultrafiltration piston-syringe using a linear positioner having sensors capable of detecting relative positions of the pistons of the replacement fluid piston-syringe and the ultrafiltration piston-syringe;
    (e) employing a first pinch valve directly connecting the replacement fluid piston-syringe to blood filtered by a hemofilter;
    (f) employing a second pinch valve directly connecting ultrafiltrate filtered out by the hemofilter to the ultrafiltration piston-syringe;
    (g) delivering the replacement fluid in the replacement fluid piston-syringe to the blood filtered by the hemofilter;
    (h) occurring simultaneously with the performance of the step (g), extracting the ultrafiltrate from the hemofilter using the ultrafiltration piston-syringe and storing the ultrafiltrate in the ultrafiltration piston-syringe;

(i) relaying information from the sensors to the first and second pinch valves regarding the relative positions of the pistons of the replacement fluid piston-syringe and the ultrafiltration piston-syringe; and (j) upon occurrence of both pistons independently reaching either a minimum or maximum stroke position, causing the first and second pinch valves to switch to an opposite state and simultaneously causing the pistons of the replacement fluid piston-syringe and the ultrafiltration piston-syringe to change directions;

(k) upon the first and second pinch valves switching to the opposite state, causing the first pinch valve to directly connect the container containing the replacement fluid to the replacement fluid piston-syringe for refilling the replacement fluid piston-syringe with the replacement fluid and simultaneously causing the second pinch valve to directly connect the ultrafiltrate piston-syringe to a container for emptying the ultrafiltrate from the ultrafiltrate piston-syringe; and (l) simultaneously refilling the replacement fluid piston-syringe with the replacement fluid and emptying the ultrafiltrate from the ultrafiltrate piston-syringe.

7. The method of claim 6, further comprising the step of continuously repeating the steps (g) through (l) for providing zero fluid balance.

8. The method of claim 6, further comprising the steps of:

(m) employing a third pinch valve directly connecting the replacement fluid flowing from the replacement fluid piston-syringe to a negative fluid balance piston-syringe;

(n) removing a portion of the replacement fluid from the replacement fluid piston-syringe and storing the removed portion of the replacement fluid in the negative fluid balance piston-syringe so that removed portion of replacement fluid does not enter the filtered blood, thereby producing a negative fluid balance; and (o) occurring simultaneously with the performance of the step (l), emptying the removed portion of the replacement fluid from the negative fluid balance piston-syringe.

9. The method of claim 8, further comprising the step of continuously repeating the steps (g) through (o).

10. A system for managing fluid for accurate continuous venovenous hemofiltration, comprising:

(a) a hemofilter configured to continuously filter unfiltered blood to extract ultrafiltrate, thereby producing filtered blood;

(b) a first container configured to be filled with replacement fluid;

(c) a second container and the first container coupled to a translating arm, wherein the translating arm is configured to move to simultaneously allow the replacement fluid to be transferred from the first container to the filtered blood and allow the ultrafiltrate to be transferred from the hemofilter to the second container, the amount of the replacement fluid and the ultrafiltrate transferred being equal to each other; and (d) at least one sensor being structurally connected to the translating arm, the sensor being configured to continuously monitor a relative position of the translating arm, thereby determining whether there is the replacement fluid contained in the first container and the ultrafiltrate contained in the second container.

11. The system of claim 10, further comprising:

a third container configured to contain a portion of the replacement fluid that is being transferred from the first container to the filtered blood so that the portion of replacement fluid transferred to the third container is not combined with the filtered blood, thereby producing a negative fluid balance between the ultrafiltrate extracted from the filtered blood and the replacement fluid transferred to the filtered blood.

12. A system for managing fluid for accurate continuous venovenous hemofiltration (CVVH) in extracorporeal membrane oxygenation, comprising:

a container configured to contain replacement fluid;

a replacement fluid piston-syringe configured to be filled with the replacement fluid, the replacement fluid piston-syringe including a piston;

an ultrafiltration piston-syringe being configured to be filled with ultrafiltrate, the ultrafiltration piston-syringe including a piston;

the replacement fluid piston-syringe and the ultrafiltration piston-syringe being coupled to a translating arm having at least one sensor capable of detecting relative positions of the pistons of the replacement fluid piston-syringe and the ultrafiltration piston-syringe;

a first pinch valve; and a second pinch valve, the first pinch and the second pinch valve being configured to switch between a first state and a second state, in the first state, the first pinch valve directly connecting the replacement fluid piston-syringe to blood filtered by a hemofilter, and the second pinch valve directly connecting the ultrafiltrate extracted by the hemofilter to the ultrafiltration piston-syringe, wherein the sensor is configured to transmit information regarding the relative positions of the pistons of the replacement fluid piston-syringe and the ultrafiltration piston-syringe to the first and second pinch valves;

wherein, upon the occurrence of both the piston of the replacement fluid piston-syringe and the piston of the ultrafiltration piston-syringe independently reaching either a minimum or maximum stroke position, the first and second pinch valves each being configured to switch to the second state and the pistons of the replacement fluid piston-syringe and the ultrafiltration piston-syringe being configured to change directions; and wherein upon the first and second pinch valves each switching to the second state, the first pinch valve being configured to directly connect the container configured to contain the replacement fluid to the replacement fluid piston-syringe and the replacement fluid piston-syringe being configured to be refilled with the replacement fluid and the second pinch valve being configured to directly connect the ultrafiltrate piston-syringe to a second container for the ultrafiltrate and the ultrafiltrate piston-syringe being configured to empty the ultrafiltrate into the second container.

13. The system of claim 12, further comprising:

a singular piston-syringe connected to the replacement fluid piston-syringe, the singular piston-syringe being configured to extract a portion of the replacement fluid being delivered to the filtered blood so that the extracted portion of replacement fluid is temporarily housed in the singular piston-syringe and is not combined with the filtered blood, thereby producing a negative fluid balance between the ultrafiltrate extracted from the filtered blood and the replacement fluid transferred to the filtered blood.

14. The method of claim 1, wherein the step (e) is performed by at least one sensor.

15. The method of claim 14, wherein the steps (a) through (h) are performed based on a position of one of a translating arm or a linear positioner coupled to the first and second containers.

16. The system of claim 10,
wherein the translating arm is configured to move between a minimum and a maximum position, and
wherein the position of the translating arm corresponds to one of a first phase or a second phase, wherein, in the first phase, the first container is configured to be refilled with additional replacement fluid at a same time as the ultrafiltrate is emptied from the second container, and wherein, in the second phase, the replacement fluid is configured to be transferred from the first container at a same time as the ultrafiltrate is extracted from the hemofilter and transferred to the second container.

17. The system of claim 16, further comprising:
a stepper drive configured to move the translating arm between the minimum and the maximum position,
wherein the stepper drive is configured to stop the translating arm and reverse the direction of the translating arm based on the position of the translating arm detected by the at least one sensor.

18. The system of 10, further comprising:
wherein the translating arm is configured so that a displacement with respect to the first container and the second container is identical.

* * * * *

UNITED STATES PATENT AND TRADEMARK OFFICE
CERTIFICATE OF CORRECTION

| | | |
|---|---|---|
| PATENT NO. | : 8,206,594 B2 | Page 1 of 1 |
| APPLICATION NO. | : 12/663253 | |
| DATED | : June 26, 2012 | |
| INVENTOR(S) | : James D. Fortenberry et al. | |

It is certified that error appears in the above-identified patent and that said Letters Patent is hereby corrected as shown below:

On the title page, item (73), Assignee, correct the name of first assignee to read as follows:

-- Emory University --

Signed and Sealed this
Thirty-first Day of July, 2012

David J. Kappos
*Director of the United States Patent and Trademark Office*